US008076107B2

(12) United States Patent
Buddoo et al.

(10) Patent No.: US 8,076,107 B2
(45) Date of Patent: Dec. 13, 2011

(54) PRODUCTION OF MONATIN STEREOISOMERS (75) Inventors: Subash Buddoo, Randburg (ZA); Amanda Louise Rousseau, Bedford Gardens (ZA); Dean Brady, Midrand (ZA); James Lalonde, Palo Alto, CA (US); Yiming Yao, West Newton, MA (US); Yifong Wang, Lexington, MA (US)

(73) Assignee: Cargill, Incorporated, Wayzata, MN (US)

( * ) Notice: Subject to any disclaimer, the term of this patent is extended or adjusted under 35 U.S.C. 154(b) by 569 days.

(21) Appl. No.: 11/865,456

(22) Filed: Oct. 1, 2007

(65) Prior Publication Data
US 2009/0087888 A1   Apr. 2, 2009

(51) Int. Cl.
*C12P 17/10* (2006.01)
*C12P 17/16* (2006.01)
*C12P 41/00* (2006.01)
(52) U.S. Cl. ......... 435/118; 435/121; 435/280; 548/497
(58) Field of Classification Search .................. None
See application file for complete search history.

(56) References Cited

U.S. PATENT DOCUMENTS

| 3,002,889 | A | 10/1961 | Kinoshita et al. |
| 3,751,458 | A | 8/1973 | Wiley |
| 3,936,472 | A | 2/1976 | Kinney et al. |
| 4,010,204 | A | 3/1977 | Koster et al. |
| 4,975,298 | A | 12/1990 | Van Wyk et al. |
| 5,128,164 | A | 7/1992 | Van Wyk et al. |
| 5,128,482 | A | 7/1992 | Olivier et al. |
| 5,545,644 | A | 8/1996 | Macor et al. |
| 5,703,270 | A | 12/1997 | Nakagawa et al. |
| 5,994,559 | A | 11/1999 | Abushanab et al. |
| 6,218,167 | B1 | 4/2001 | Allen et al. |
| 6,264,999 | B1 | 7/2001 | Yatka et al. |
| 6,277,626 | B1 * | 8/2001 | Hansen et al. ............... 435/280 |
| 6,489,100 | B1 | 12/2002 | Liao |
| 6,743,910 | B2 | 6/2004 | Cimpoia et al. |
| 7,064,219 | B2 | 6/2006 | Kawahara et al. |
| 7,081,359 | B2 | 7/2006 | Lim |
| 7,354,746 | B1 | 4/2008 | Suzuki et al. |
| 7,396,941 | B2 | 7/2008 | Mori et al. |
| 7,534,898 | B2 | 5/2009 | Amino et al. |
| 7,781,005 | B2 | 8/2010 | Mori |
| 7,816,541 | B2 | 10/2010 | Kawahara et al. |
| 7,888,081 | B2 | 2/2011 | Khare et al. |
| 2003/0228403 | A1 | 12/2003 | Amino et al. |
| 2004/0063175 | A1 | 4/2004 | Abraham et al. |
| 2005/0004394 | A1 | 1/2005 | Kawahara et al. |
| 2005/0009153 | A1 | 1/2005 | Sugiyama et al. |
| 2005/0020508 | A1 | 1/2005 | Amino et al. |
| 2005/0106305 | A1 | 5/2005 | Abraham et al. |
| 2005/0112260 | A1 | 5/2005 | Abraham et al. |
| 2005/0118317 | A1 | 6/2005 | Amino et al. |
| 2005/0137246 | A1 | 6/2005 | Amino et al. |
| 2005/0153405 | A1 | 7/2005 | Sugiyama et al. |
| 2005/0170041 | A1 | 8/2005 | Abraham et al. |
| 2005/0221452 | A1 | 10/2005 | Takagi et al. |
| 2005/0221455 | A1 | 10/2005 | McFarlan et al. |
| 2005/0244937 | A1 | 11/2005 | Abraham et al. |
| 2005/0244939 | A1 | 11/2005 | Sugiyama et al. |
| 2005/0272939 | A1 | 12/2005 | Amino et al. |
| 2005/0282260 | A1 | 12/2005 | Hicks et al. |
| 2006/0003411 | A1 | 1/2006 | Sugiyama et al. |
| 2006/0003426 | A1 | 1/2006 | Sugiyama et al. |
| 2006/0009394 | A1 | 1/2006 | Amino |
| 2006/0014819 | A1 | 1/2006 | Mori et al. |
| 2006/0074249 | A1 | 4/2006 | Kawahara et al. |
| 2006/0083695 | A1 | 4/2006 | Mori |
| 2006/0154343 | A1 | 7/2006 | Mori et al. |
| 2006/0172396 | A1 | 8/2006 | Sugiyama et al. |
| 2006/0252135 | A1 | 11/2006 | Brazeau et al. |
| 2007/0099277 | A1 | 5/2007 | Anderson et al. |
| 2007/0105938 | A1 | 5/2007 | Anderson et al. |
| 2008/0020434 | A1 | 1/2008 | Brazeau et al. |
| 2008/0020435 | A1 | 1/2008 | Burke et al. |
| 2008/0274518 | A1 | 11/2008 | Hicks et al. |
| 2009/0087829 | A1 | 4/2009 | Brady et al. |
| 2009/0088577 | A1 | 4/2009 | Buddoo et al. |
| 2009/0117625 | A1 | 5/2009 | Abraham et al. |
| 2009/0130285 | A1 | 5/2009 | Abraham et al. |
| 2009/0198072 | A1 | 8/2009 | Khare et al. |
| 2010/0221795 | A1 | 9/2010 | Takakura et al. |
| 2011/0020882 | A1 | 1/2011 | de Souza et al. |
| 2011/0045547 | A1 | 2/2011 | de Souza et al. |

FOREIGN PATENT DOCUMENTS

| EP | 0 438 314 | * | 4/1994 |
| EP | 1 045 029 | * | 10/2000 |
| EP | 1 350 791 | * | 10/2003 |
| EP | 1 445 323 | * | 8/2004 |
| EP | 1 449 832 | * | 8/2004 |
| EP | 1 533 376 | * | 5/2005 |
| EP | 1 580 268 | * | 9/2005 |
| EP | 1 605 041 | * | 12/2005 |
| EP | 1 719 758 | * | 11/2006 |
| JP | 2002-060382 | * | 2/2002 |
| JP | 2003-171365 | * | 6/2003 |
| JP | 2004-222657 | * | 8/2004 |

(Continued)

OTHER PUBLICATIONS

Ackerman, "Structure elucidation of and synthetic approaches to monatin, a metabolite from *Schlerochiton ilicifolius*," PhD dissertation, University of Stellenbosch, Jul. 1990.* Ager et al., "Commercial, Synthetic Nonnutritive Sweeteners," *Agnew. Chem. Int. Ed.*, 1998, 37:1802-1817.*

Ager et al., "Novel biosynthetic routes to non-proteinogenic amino acids as chiral pharmaceutical intermediates," *Journal of Molecular Catalysis B: Enzymatic*, 2001, 11:199-205.*

Azuma et al., "Hyper-production of L-tryptophan via fermentation with crystallization," *Appl. Microbiol. Biotechnol.*, 1993, 39:471-476.*

Bae et al., "Production of aromatic D-amino acids from α-keto acids and ammonia by coupling of four enzyme reactions," *Journal of Molecular Catalysis B: Enzymatic*, 1999, 6:241-247.*

(Continued)

*Primary Examiner* — Herbert J. Lilling (57) ABSTRACT

Methods and materials for the production of the high intensity sweetener, monatin, in stereoisomerically-pure or stereoisomerically-enriched form are disclosed. For example, methods using stereoisoselective hydrolysis and separation of a monatin-derived lactone ester are disclosed.

8 Claims, 5 Drawing Sheets

FOREIGN PATENT DOCUMENTS

| | | | |
|---|---|---|---|
| JP | 2004-331644 | * | 11/2004 |
| JP | 2004-331650 | * | 11/2004 |
| WO | WO 89/11212 | | 11/1989 |
| WO | WO 03/045914 | | 6/2003 |
| WO | WO 03/056026 | | 7/2003 |
| WO | WO 03/059865 | | 7/2003 |
| WO | WO 03/091396 | | 11/2003 |
| WO | WO 2005/001105 | | 1/2005 |
| WO | WO 2005/014839 | | 2/2005 |
| WO | WO 2005/016022 | | 2/2005 |
| WO | WO 2005/020721 | | 3/2005 |
| WO | WO 2005/042756 | | 5/2005 |
| WO | WO 2005/082850 | | 9/2005 |
| WO | WO 2006/011613 | | 2/2006 |
| WO | WO 2006/113897 | | 10/2006 |
| WO | WO 2006/116487 | | 11/2006 |
| WO | WO 2007/103389 | | 9/2007 |
| WO | WO 2007/133183 | | 11/2007 |
| WO | WO 2007/133184 | * | 11/2007 |
| WO | WO2010/105014 | | 9/2010 |
| WO | WO2010/138513 | | 12/2010 |

OTHER PUBLICATIONS

Bassoli, "'Chemistry-Nature,' still an open match for the discovery of new intensive sweeteners," *Agro FOOD industry hi-tech*, 2004, 15(4):27-29.*

Bassoli et al., "Design and synthesis of new monatin derivatives," *Abstracts, 13th International Symposium on Olfaction and Taste (ISOT XIII), 14th. European Chemoreception Research Organization Congress (ECRO XIV)*, Jul. 20-24, 2000, p. 162.*

Bassoli et al., "General Pseudoreceptor Model for Sweet Compounds: A Semiquantitative Prediction of Binding Affinity for Sweet-Tasting Molecules," *J. Med. Chem.*, 2002, 45:4402-4409.

Bassoli et al., "Monatin and Its Stereoisomers: Chemoenzymatic Synthesis and Taste Properties," *Eur. J. Org. Chem.*, 2005, 8:1652-1658.

Bhatnagar et al., "The Broad-specificity, Membrane-bound Lactate Dehydrogenase of *Neisseria gonorrhoeae*: Ties to Aromatic Metabolism," *J. Gen. Microbiol.*, 1989, 135:353-360.

Bommarius et al., "Some new developments in reductive amination with cofactor regeneration," *Biocatalysis*, 1994, 10:37-47.

Bongaerts et al., "Metabolic Engineering for Microbial Production of Aromatic Amino Acids and Derived Compounds," *Metabolic Engineering*, 2001, 3:289-300.

Brandl and Lindow, "Cloning and characterization of a locus encoding an indolepyruvate decarboxylase involved in indole-3-acetic acid synthesis in *Erwinia herbicola*," *Appl. Environ. Microbiol.*, 1996, 62:4121-4128

Camargo (Ediclea Cristina Fregonese Camargo), "Preparation of amino acids not proteinogênicos, structurally related to adoçante natural Monatina" [translated by Google], Jan. 2003, Universidade Estadual de Campinas Instituto de Quimica, Dissertation of Masters.

Curran, "Reduction of .DELTA.2-isoxazolines: a conceptually different approach to the formation of aldol adducts," *J. Am. Chem. Soc.*, 1982, 104:4024-4026.

DeLuna et al., "NADP-Glutamate Dehydrogenase Isoenzymes of *Saccharomyces cerevisiae*:Purification, Kinetic Properties, and Physiological Roles," *J. Biol. Chem.*, 2001, 276(47):43775- 43783.

Floyd et al., "A Simple Strategy for obtaining both Enantiomers from an Aldolase Reaction: Preparation of L- and D-4-Hydroxy-2-ketoglutarate," *J. Chem. Soc. Perkin Trans. 1*, 1992, 1085-1086.

Henderson et al., "Stereospecific Preparation of the N-Terminal Amino Acid Moiety of Nikkomycins KX and KZ via a Multiple Enzyme Synthesis," *J. Org. Chem.*, 1997, 62:7910-7911.

Holzapfel et al., "A simple cycloaddition approach to a racemase of the natural sweetener monatin," *Synthetic Communications*, 1994, 24(22):3197-3211.

Holzapfel et al., "The synthesis of a gamma-keto-alpha-amino acid, a key intermediate in the synthesis of monatin, a new natural sweetener," *Synthetic Communications*, 1993, 23(18):2511-2526.

Izumi, "Introduction," *Synthetic Production and Utilization of Amino Acids*, 1974, Kankeko et al. (eds.), Halstad Press, Chapter 1, pp. 3-16.

Juhl et al., "Catalytic asymmetric homo-aldol reaction of pyruvate—a chiral Lewis acid catalyst that mimics aldolase enzymes," *Chem. Commun.*, 2000, 2211-2212.

Kogiso et al., "Control of Lactamization during the Synthesis of the Monatin Analogue," *Peptide Science*, 2003, pp. 195-198.

Kogiso et al., "The C-C Bond Formation with Alkyl Halide in Monatin Analogue Synthesis and Their Tastes Expression," *Peptide Science*, 2004, Shimohigashi (ed.), Japanese Peptide Society, pp. 165-168.

Li et al., "Nonproteinogenic alpha-Amino Acid Preparation Using Equilibrium Shifted Transamination," *Organic Process Research & Development*, 2002, 6:533-538.

Nakamura et al., "Total Synthesis of Monatin," *Organic Letters*, 2000, 2(19):2967-2970.

Nakamura et al., "Total Synthesis of Monatin and the Taste Experience," *Peptide Science*, 2003, pp. 61-64.

Oliveira et al., "Highly diastereoselective alkylation of a pyroglutamate derivative with an electrophile obtained from indole. Synthesis of a potential intermediate for the preparation of the natural sweetener (−)-monatin," *Synthetic Communications*, 2000, 30(12):2143-2159.

Oliveira et al., "Diastereoselective formation of a quaternary center in a pyroglutamate derivative. Formal synthesis of Monatin," *Tetrahedron Letters*, 2001,42:6793-6796.

Tamura et al., "Highly stereoselective synthesis of (−)-monatin, a high-intensity sweetener, using chelation-controlled nitrone cycloaddition," *Chemical Communications*, 2003, 21:2678-2679.

Tamura et al., "Stereoselective Synthesis of 4-Hydroxy 4-Substituted Glutamic Acids," *J. Org. Chem.*, 2005, 70(12):4569-77.

Vleggaar et al., "Structure elucidation of monatin, a high-intensity sweetener isolated from the plant *Schlerochiton ilicifolius*," *J. Chem. Soc. Perkin Transactions 1: Organic and Bio-Organic Chemistry* (1972-1999), 1992, 22:3095-3098.

Wolf et al., "A Biocatalytic Route to Enantiomerically Pure Unsaturated -H—Amino Acids," *Adv. Synth. & Catalysis*, 2001, 343:662-674.

Buldain et al., "Carbon-13 Nuclear Magnetic Resnoance Spectra of the Hydrate, Keto, and Enol Forms of Oxalacetic Acid," *Magnetic Resonance Chemistry*, 1985, 23(6):478-481.

Gosset et al., "A direct comparison of approaches for increasing carbon flow to aromatic biosynthesis in *Escherichia coli*," *Journal of Industrial Microbiology*, 1996, 17:47-52.

Guo et al., "Protein tolerance to random amino acid charge," *Proc. Natl. Acad. Sci. USA*, 2004, 101(25):9205-9210.

Seffernick et al., "Melamine deaminase and atrazine chlorohydrolase: 98 percent identical but functionally different," *J. Bacteriology*, 2001, 183(8):2405-2410.

Seo Jeong-Sun et al., "The genome sequence of the ethanologenic bacterium *Zymomonas mobilis* ZM4," *Nature Biotechnology*, 2005, 23(1):63-68.

Whisstock et al., "Prediction of protein function from protein sequence," *Q. Rev. Biophysis*, 2003, 36(3):307-340.

Witkowski et al., "Conversion of b-ketoacyl synthase to a malonyl decarboxylase by replacement of the active-site cysteine with glutamine," *Biochemistry*, 1999, 38:11643-11650.

Chica et al., "Semi-rational approaches to engineering enzyme activity: combining the benefits of directed evolution and rational design", *Current Opinion in Biotechnology*, 2005, 16:378-384.

Curran et al., "Reduction of .DELTA.2-isoxazolines. 3. Raney nickel catalyzed formation of .beta.-hydroxy ketones," *J. Am. Chem. Soc.*, 1983, 105:5826-5833.

Fuganti et al., "Kinetic resolution of substituted 1,3-4H-5,6-Dihydrooxazines with carboxylesterase NP", *Bioorganic and Medicinal Chemistry*, 1994, vol. 2, 7:723-726.

Moriya et al., "A facile synthesis of 6-chloro-D-tryptophan" *Bulletin of the Chemical Society of Japan*, 1975, 48:2217-2218 (abstract).

"Cross-Linked Crystals of Subtilisin Versatile Catalysts for Organic Synthesis", Yi-Fong Wang, et al., Altus Biologics Incorporated, pp. 777-783 (XP 002041055).

* cited by examiner

PRODUCTION OF MONATIN STEREOISOMERS

FIELD OF THE INVENTION

The present invention is in the field of organic and biocatalytic synthesis.

BACKGROUND

Monatin is a high-intensity sweetener having the chemical formula:

Because of various naming conventions, monatin is also known by a number of alternative chemical names, including: 2-hydroxy-2-(indol-3-ylmethyl)-4-aminoglutaric acid; 4-amino-2-hydroxy-2-(1H-indol-3-ylmethyl)-pentanedioic acid; 4-hydroxy-4-(3-indolylmethyl)glutamic acid; and 3-(1-amino-1,3-dicarboxy-3-hydroxy-but-4-yl)indole.

Monatin contains two chiral centers leading to four potential stereoisomeric configurations. The R,R configuration (the "R,R stereoisomer" or "(R,R)-monatin"); the S,S configuration (the "S,S stereoisomer" or "(S,S)-monatin"); the R,S configuration (the "R,S stereoisomer" or "(R,S)-monatin"); and the S,R configuration (the "S,R stereoisomer" or "(S,R)-monatin"). The different stereoisomers of monatin have different sweetening characteristics.

Certain isomeric forms of monatin can be found in the bark of roots of the *Schlerochiton ilicifolius* plant located predominately in the Limpopo region, but also in Mpumalanga and the North West Province of South Africa. However, the concentration of the monatin present in the dried bark, expressed as the indole in its acid form, has been found to be about 0.007% by mass. See U.S. Pat. No. 4,975,298. The exact method by which monatin is produced in the plant is presently unknown.

At least in part because of its sweetening characteristic, it is desirable to have an economic source of monatin. Furthermore, because of the different sweetening characteristics of the different stereoisomers, it is desirable to have an economic source of a single stereoisomer of monatin, such as the R,R stereoisomer. Thus, there is a continuing need to develop methods for the production of monatin in stereoisomerically-pure or stereoisomerically-enriched form.

SUMMARY

The invention provides methods for resolving isomeric forms of the high intensity sweetener, monatin, and particularly resolving the R,R and S,S stereoisomers of monatin. In some embodiments of the invention, an ester derivative of monatin is produced and stereoisoselective hydrolysis of the monatin-derived ester results ultimately in stereoisomerically-pure or stereoisomerically-enriched monatin. In some embodiments, the stereoisoselective hydrolysis preferentially converts one stereoisomeric form of the monatin-derived ester (for example S,S) over another stereoisomeric form of the monatin-derived ester (for example R,R) to a monatin-derived acid (for example S,S). The monatin-derived acid (for example S,S) and monatin-derived ester (for example R,R) can then be separated, and once separated each can then be converted back to monatin resulting in a composition of stereoisomerically-pure or stereoisomerically-enriched S,S monatin and a composition of stereoisomerically-pure or stereoisomerically-enriched R,R monatin. In some embodiments, a lactone ester derivative of monatin is produced, and one stereoisomeric form of the lactone ester derivative is stereospecifically hydrolyzed using an enzyme. The hydrolyzed product of the reaction can then be separated from the non-hydrolyzed ester derivative and each of the hydrolyzed and non-hydrolyzed derivatives can be converted back to monatin.

The specification, including the figures, describe certain embodiments of the invention. A person of ordinary skill should realize, however, from the description therein that the invention is capable of modifications in various aspects, all without departing from the spirit and scope of the invention. Accordingly, the specification and figures are to be regarded as illustrative in nature and not restrictive.

DESCRIPTION

This disclosure provides methods for resolving the (R,R) and (S,S) stereoisomers of glutamic acid derivatives, especially monatin. Each reference herein to a molecule containing chiral centers, refers to all isomeric forms of the molecule, unless otherwise specified. Although each isomer is a distinct compound, in practice a mixture of stereoisomers is often referred to as "a compound", such as e.g., "the compound (±)-monatin precursor" or "monatin precursor." Similarly, each structural depiction of a molecule herein containing chiral centers represents all isomeric forms of the molecule, unless otherwise specified, for example through use of wedge diagrams to show three-dimensional conformation.

Also, unless otherwise specified or unless otherwise clear from the context, references to "R,R monatin" or "S,S monatin" mean the single stereoisomer of monatin or a mixture enriched in the specified stereoisomer. "Enriched" means that the mixture includes a higher ratio of designated stereoisomer to non-designated stereoisomer as compared to the original monatin mixture from which it was resolved.

A single stereoisomer can be differentiated from a stereoisomerically-enriched mixture of stereoisomers by referring to the former as a "single stereoisomer." Thus, for example, unless otherwise specified or unless otherwise clear from the context, "(S,S)-monatin" indicates the single stereoisomer of monatin with S configuration at each stereogenic center, or a mixture of (S,S)-monatin and (R,R)-monatin in which (S,S)-monatin is present in greater amount.

Additionally, each compound formula designated with a Roman numeral followed by a lower case letter will herein designate a single stereoisomer or a mixture enriched in that stereoisomer. For example, reference to "a compound" of Formula IV:

IV(±)

refers to an isomeric mixture of the compound shown. (The use of "(±)" is included for clarity to designate that the indicated formula includes a mixture of isomeric forms.) Similarly, reference to "a compound" of Formula IVa:

IVa(R,R)

refers to both the single stereoisomer shown and to a mixture enriched in that stereoisomer, unless otherwise specified or unless otherwise clear from the context, wherein the ratio of R,R to S,S isomer is higher in the mixture represented by IVa (R,R) than the mixture represented by IV (±). (The use of "(R,R)" is included for clarity to designate that the indicated formula represents the R,R stereoisomer or a mixture enriched in the R,R stereoisomer.) Typically, for the compounds described herein, the letter "a" will designate formulas having an R,R configuration, and "b" will designate formulas having an S,S configuration.

Unless otherwise specified, the terms "include," "includes," "including" and the like are intended to be open-ended. Thus, for example, "include" means "include but are not limited to."

Except as otherwise noted, the articles "a," "an," and "the" mean "one or more."

As used herein, the term "about" encompasses the range of experimental error that occurs in any measurement. Unless otherwise stated, all measurements are presumed to have the word "about" in front of them even if the word "about" is not expressly used.

The term "alkyl" as employed herein by itself or as part of another group refers to both straight and branched chain saturated radicals of up to 10 carbons, unless the chain length is otherwise limited, such as methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl, nonyl, decyl and the like.

Figure 1:
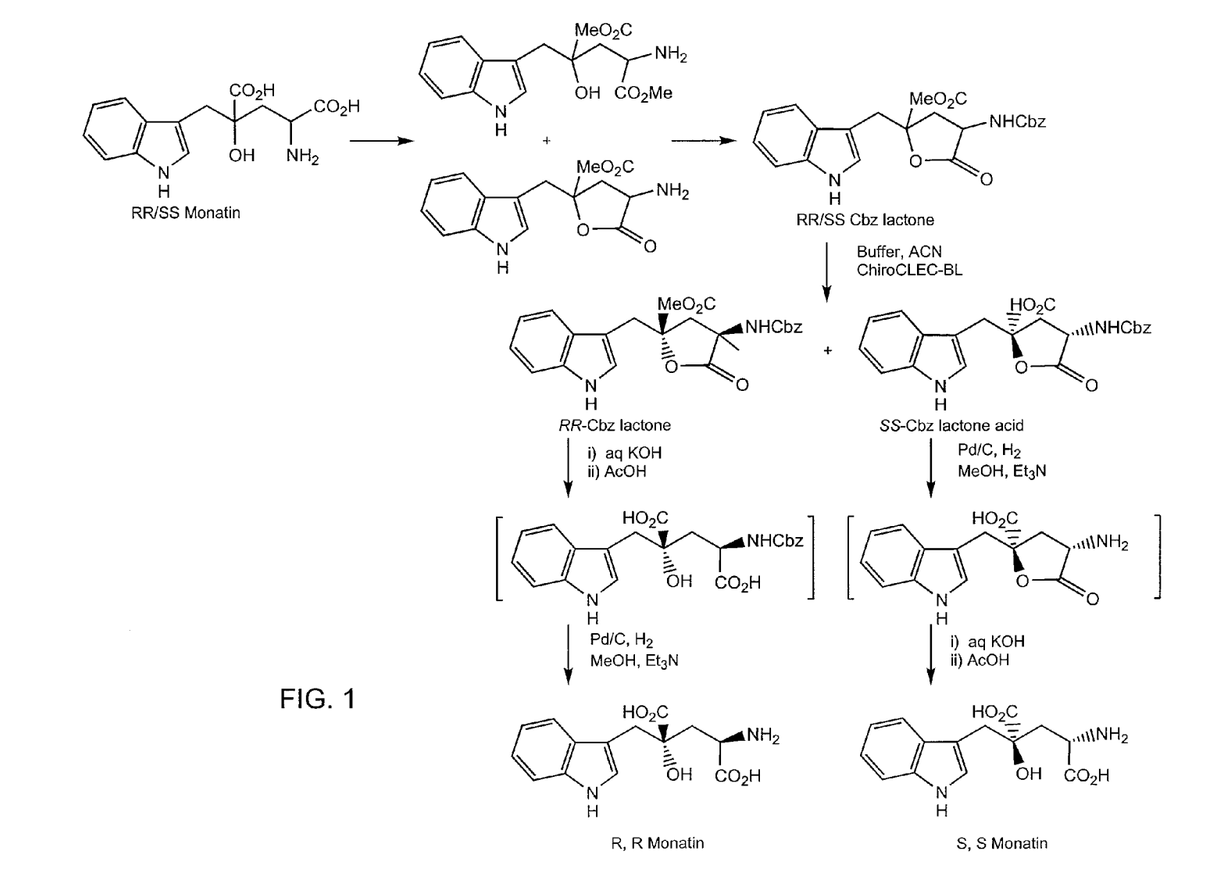
FIG. 1 illustrates a reaction scheme for separating the (R,R) and (S,S) stereoisomers of monatin in accordance with an embodiment of the invention.
Figure 2:
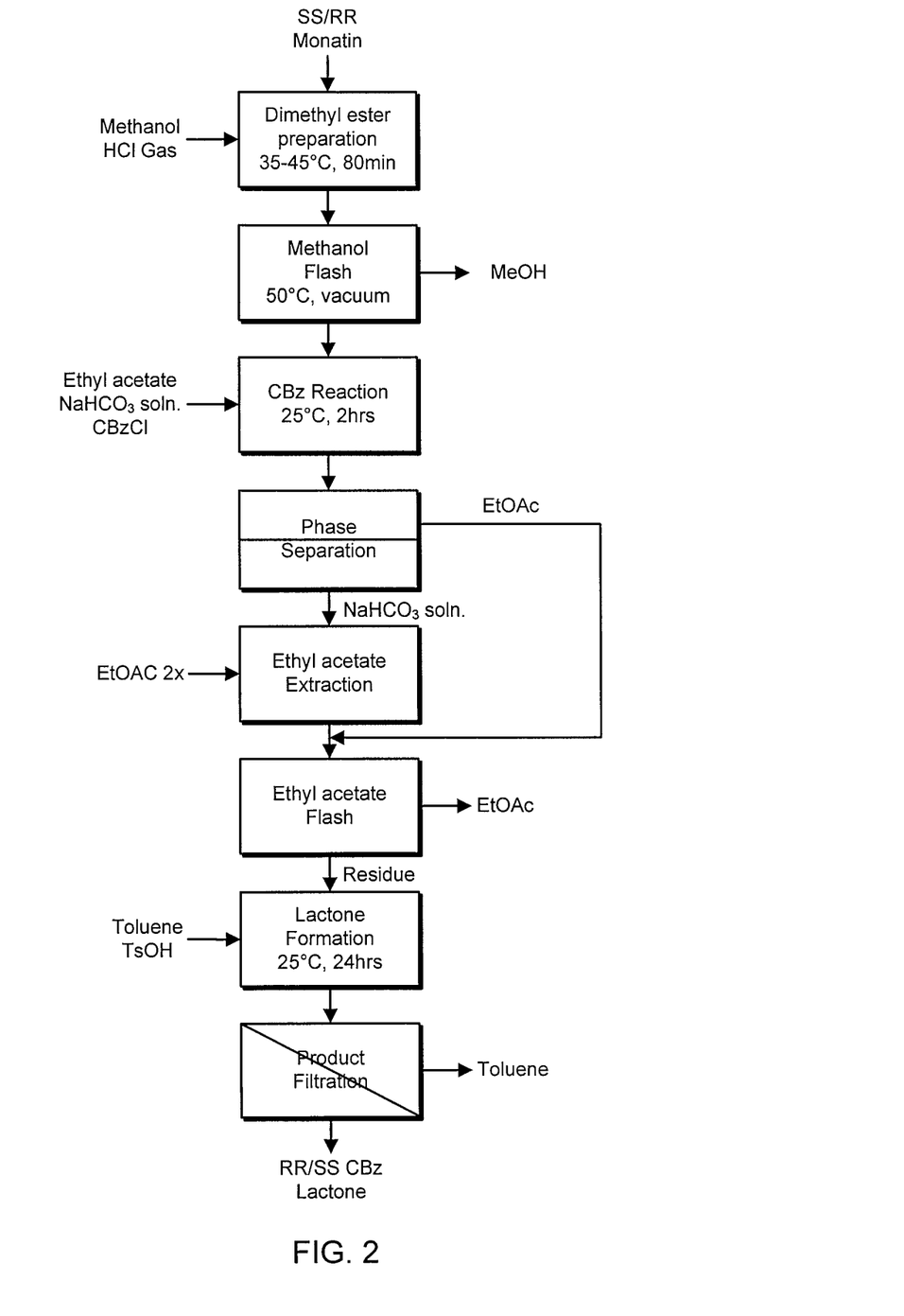
FIG. 2 is a schematic of a process for protecting the amine function in a monatin-derived compound and generating a lactone in accordance with an embodiment of the invention.

Referring now to the Figures, FIG. 1 illustrates a method for resolving a mixture of R,R and S,S stereoisomeric pairs of monatin. In accordance with the embodiment, monatin, and specifically a monatin composition of R,R and S,S monatin, is reacted to ultimately generate a protected lactone ester derivative of monatin, and specifically a mixture of R,R and S,S monatin-derived lactone esters. As depicted, the lactone ester monatin derivative is generated in a multi-step process, wherein initially a diester derivative of monatin and a lactone ester derivative of monatin are formed. FIG. 2 illustrates more specific details of an embodiment for carrying out the formation of the monatin lactone ester derivative from monatin.

The mixture produced in the esterification reaction (the lactone ester and diester derivatives of monatin) can then be exposed to reaction conditions suitable for converting the diester derivative to the lactone ester derivative. In accordance with some embodiments, it is preferable to convert as much of the diester derivative as possible into the lactone ester derivative; this is particularly the case where the enzyme chosen to perform the stereospecific hydrolysis reacts preferentially or only on the lactone form.

Preferably, and in accordance with the embodiment shown in FIG. 1, the amine functionality of the lactone ester monatin derivative is protected prior to undergoing enzymatic hydrolysis. Protection of the amine functionality can be accomplished by any means known in the art, for example by Cbz protection. Example 2 provides details for some methods for Cbz protection of the monatin amine functionality.

The lactonisation reaction can be carried out under alternative reaction conditions, for example as show in Example 3a and 3b. Other conditions are also suitable for lactonisation to occur. For example, in some embodiments, trifluoroacetic acid may be used in place of or in addition to the toluene sulfonic acid. Preferably, lactonisation is carried out at about room temperature, or from about 23 to about 25 degrees C. Without being bound by theory, it is believed that high temperatures, such as about 65 degrees C. can lead to decomposition, and therefore require additional steps such as the use of column chromatography to recover the desired products.

Figure 3:
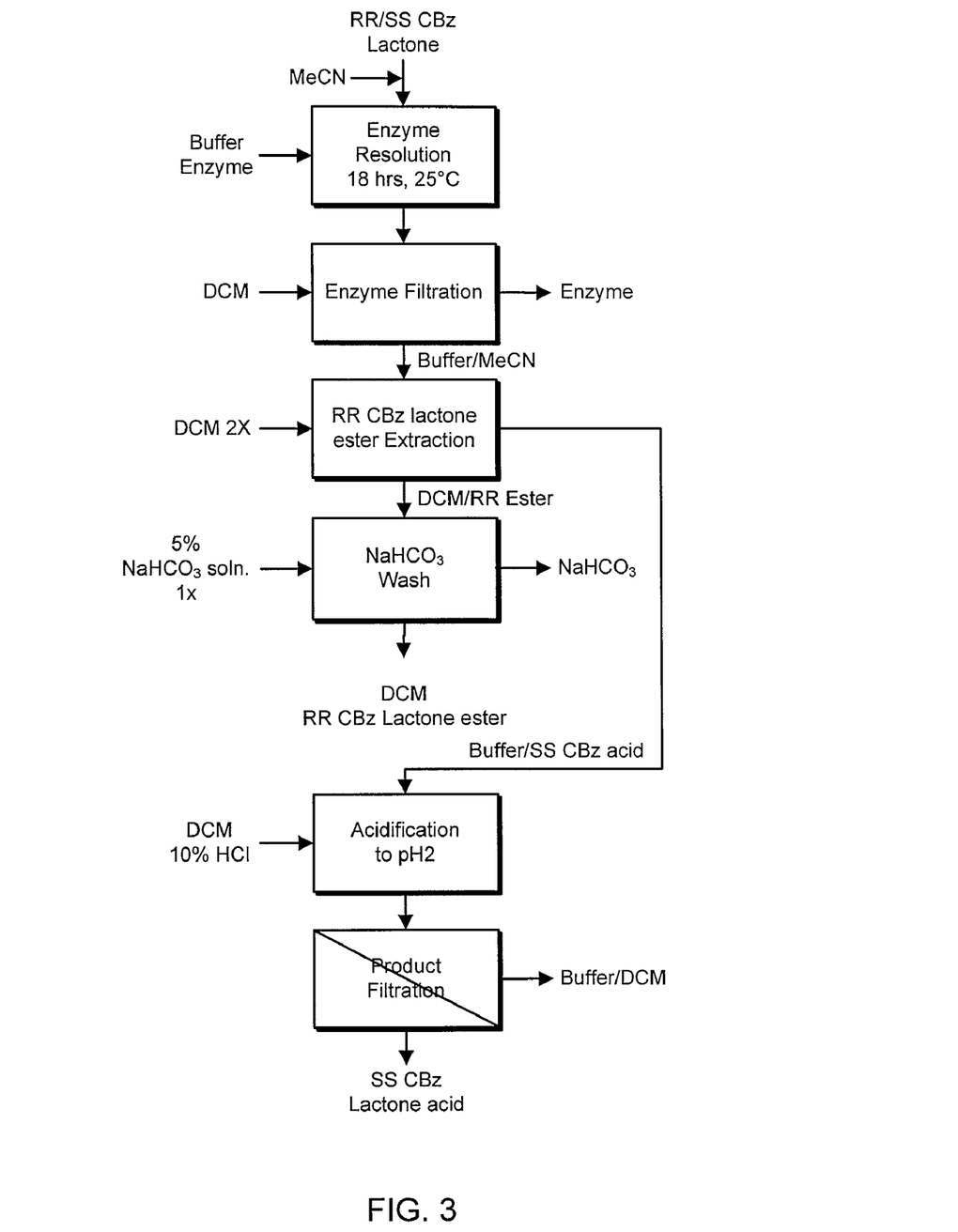
FIG. 3 is a schematic of a process for enzymatically resolving (R,R) and (S,S) stereoisomers in accordance with an embodiment of the invention.

Next, the monatin-derivative stereoisomeric mixture undergoes stereospecific hydrolysis. More particularly, hydrolysis of an ester functionality of the monatin derivative to an acid functionality occurs preferentially for one isomer form over another. Without being bound by theory, it is believed, as shown in FIG. 1, that the alkylester carboxy function is involved in the hydrolysis reaction. The hydrolysis results in a stereoisomerically-pure or stereoisomerically-enriched S,S form of the protected lactone carboxylic acid derivative and a stereoisomerically-pure or stereoisomerically-enriched R,R form of the protected carboxylic ester derivative, which can then be separated, for example by phase separation as shown in Example 4 and FIG. 3.

Figure 4:
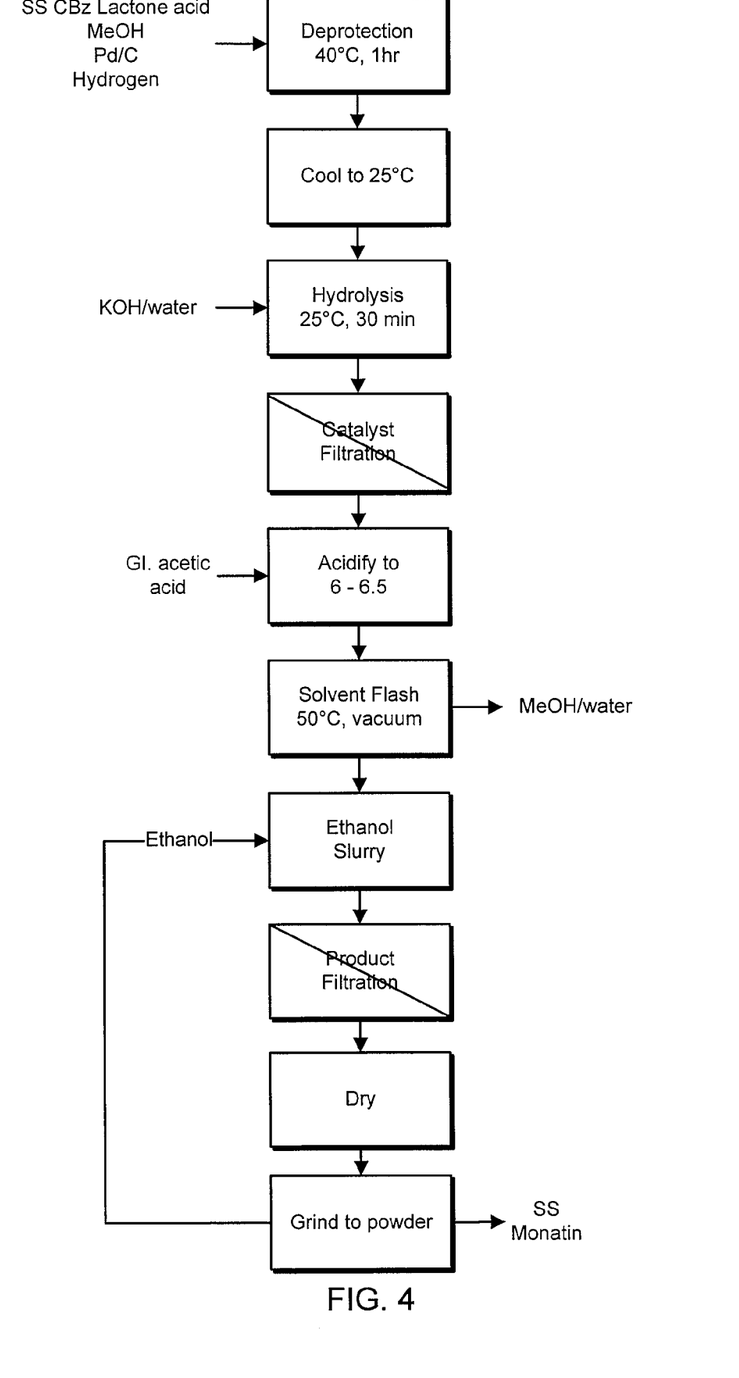
FIG. 4 is a schematic of a process for converting an (S,S) monatin derivative to monatin in accordance with an embodiment of the invention.
Figure 5:
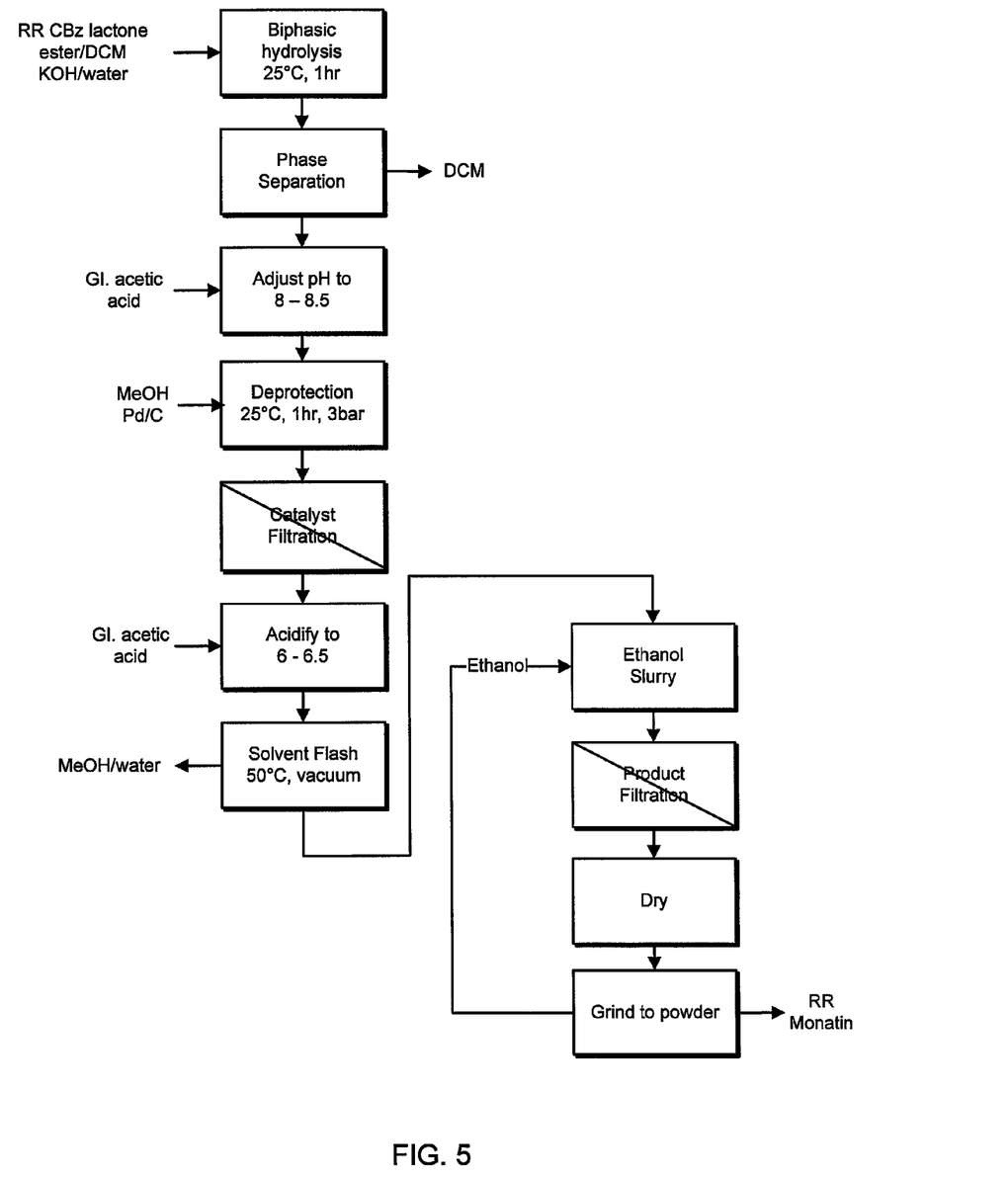
FIG. 5 is a schematic of a process for converting an (R,R) monatin derivative to monatin in accordance with an embodiment of the invention.

After separation, the S,S protected lactone derivate can be worked up to regenerate S,S monatin (either stereoisomerically-pure or stereoisomerically-enriched) and the R,R protected lactone derivative can be worked up to regenerate R,R monatin (either stereoisomerically-pure or stereoisomerically-enriched). The work up involves both a hydrogenation reaction to deprotect the derivative and a hydrolysis reaction to break the lactone ring and regenerate the original substrate, in this case monatin. In some embodiments, particularly where the S,S conformation is the substrate, it is preferable to perform the hydrogenation reaction prior to the hydrolysis reaction (in order to alleviate or minimize epimerization which can scramble the stereochemistry). In some embodiments, particularly where the R,R form is involved hydrolysis is performed prior to hydrogenation to avoid or alleviate generation of lactams. FIG. 4 and Example 5 illustrate methods for converting the S,S lactone derivative to S,S monatin. FIG. 5 and Example 6 illustrate methods for converting the R,R lactone derivative to R,R monatin.

Although embodiments directed to resolution of R,R and S,S monatin stereoisomers have been described, the invention should not be so limited. A person of skill in the art will recognize from the teachings herein that the separation process can be applied to other compounds in addition to monatin. For example, the invention encompasses a process comprising: hydrolyzing a compound of Formula IV:

IV(±)

wherein:
$R^1$ is $C_{1-10}$ alkyl; and
—N(H)Prot is a protected amino group;
to form a compound of Formula Vb:

Vb(S,S)

and a compound of Formula IVa:

IVa(R,R)

The compounds of Formula Vb and IVa are useful in the production of (S,S)-monatin and (R,R)-monatin, respectively.

Useful values of $R^1$ include $C_{1-10}$ alkyl, particularly $C_{1-6}$ alkyl, more particularly $C_{1-4}$ alkyl. Examples of useful values of $R^1$ include methyl, ethyl, propyl, isopropyl and butyl, especially methyl and ethyl. In some embodiments, $R^1$ is methyl.

Useful values of —N(H)Prot include any protected amino group (1) that is essentially unreactive under the conditions employed in the reaction under consideration, (2) that essentially does not interfere with the progress of the reaction under consideration, and (3) that can be removed under conditions that essentially will not affect the integrity of the molecule. Protected amino groups are well known to those of ordinary skill in the art and are described in, e.g., T. W. Greene and P. G. M. Wuts, *Protective Groups in Organic Synthesis,* 3rd ed., New York: John Wiley & Sons, Inc., 1999 ("Greene"), particularly at pages 494-615. The H in —N(H)Prot is present when Prot is a monoradical, e.g., when Prot is benzyl, then —N(H)Prot is —NHBn (Bn=benzyl). When Prot is a diradical, e.g., when Prot is benzylidene, the H in —N(H)Prot is not present.

Examples of useful values of —N(H)Prot include amino groups protected as groups that can be cleaved by $H_2$/cat., e.g., $H_2$/Raney (Ni); $H_2$/Pt, pH 2-4; $H_2$/Pd; $H_2$/Lindlar; or $H_2$/Rh. Examples of such protected amino groups include an amino group protected as a carbamate such as a 1,1-dimethylpropynyl, 1-methyl-1-phenylethyl, 1-methyl-1-(4-biphenyl)ethyl, t-butyl, vinyl, allyl, cinnamyl, N-hydroxypiperidinyl, 4,5-diphenyl-3-oxazolin-2-one, benzyl, p-nitrobenzyl, 3,4-dimethoxy-6-nitrobenzyl, 2,4-dichlorobenzyl, 5-benzisoxazolylmethyl, 9-anthrylmethyl, diphenylmethyl, isonicotinyl or S-benzyl carbamate, or the like; an amino group protected as an amide such as an N-formyl, N-o-nitrophenylacetyl, N-2-methyl-2-(o-nitrophenoxy)propionyl, N-2-methyl-2-(o-phenylazophenoxy)propionyl or N-o-nitrocinnamoyl amide, or the like; and —N(H)Prot wherein Prot is allyl, benzyloxymethyl, tetrahydropyranyl, benzyl, o-nitrobenzyl, di(p-methoxyphenyl)methyl, triphenylmethyl, (p-methoxyphenyl)diphenylmethyl, diphenyl-4-pyridylmethyl, benzylidene, nitro, benzylsulfonyl or phenacylsulfonyl, or the like. In some embodiments, —N(H)Prot is —NHCbz (Cbz=benzyloxycarbonyl, i.e., the amino group is protected as a benzyl carbamate).

In some embodiments, the compound of Formula IV may be formed by protecting a compound of Formula III

III

Useful reagents for effecting this protection are well known to those of ordinary skill in the art and are described in, e.g., Greene, supra, particularly at pages 494-615. In some embodiments, the compound of Formula III is protected using CbzCl, affording a compound of Formula IV in which —N(H)Prot is —NHCbz.

The compound of Formula III may be made by any suitable means. For example, U.S. Pat. No. 5,994,559 reports a synthesis of a compound of Formula III via ring-opening of an epoxide intermediate. Alternatively, the compound of Formula IV (wherein $R^1$=methyl and Prot=Cbz) may be formed from monatin, for example as described above or as illustrated in Scheme 2, below, but compounds of Formula IV with other useful values of $R^1$ and Prot may be made analogously.

In addition to the reagents exemplified above for carrying out the esterification and lactonisation conversions, other useful reagents and conditions for carrying out these conversions may be used, for example as described in Greene, supra, particularly at pages 494-615 (amino protection); M. B. Smith and J. March, *March's Advanced Organic Chemistry*, 5th ed., New York: John Wiley & Sons, Inc., 2001 ("March"), particularly at pages 484-90 (esterification of carboxylic acid, transesterification); and R. C. Larock, *Comprehensive Organic Transformations*, 2d ed., John Wiley & Sons, Inc.: New York (1999) ("Larock"), particularly at pages 1861-1927 (lactone formation) and 1932-41 (esterification of carboxylic acid).

It will be apparent to one of ordinary skill in the art that the compound of Formula IVa is "formed" from the compound of Formula IV by depletion of the other stereoisomer. That is, if the compound of Formula IV is recognized as the mixture of the compound of Formula IVa and the compound of Formula IVb (for example, a racemic mixture of the compound of Formula IVa and the compound of Formula IVb) then a preferential conversion of IVb to Vb results in enrichment of the starting racemate in the unhydrolyzed stereoisomer. Thus, the starting racemate IV becomes a "compound of Formula IVa" using the previously described nomenclature.

One of ordinary skill in the art will also appreciate that few, if any, stereospecific reactions perfectly discriminate between stereoisomers. Thus, hydrolysis of a compound of Formula IV may result in the formation of a compound of Formula Va:

Va(R,R)

via undesired hydrolysis of IVa. Such a result is contemplated by the present invention, provided that the amount of the single stereoisomer of Formula Va formed is less than the amount of the single stereoisomer of Formula Vb formed. Similarly, the product mixture may include a compound of the Formula IVb, for example due to incomplete hydrolysis.

Hydrolysis of the compound of Formula IV may be accomplished enzymatically or non-enzymatically. Enzymatic hydrolysis may be accomplished using, e.g., an enzyme such as a hydrolase (E.C. 3.-.-.-) that is capable of catalyzing a reaction that utilizes a carboxylic ester as a substrate (as exemplified by the carboxylic ester shown in Formula IV) and $H_2O$ to produce, as a product, a carboxylate (as exemplified by Formula Va). Examples of hydrolases include esterases (EC 3.1.-.-), lipases and proteases. In some embodiments, the enzyme, ChiroCLEC-BL (Altus Biologics, Inc., Cambridge, Mass.). In some embodiments the enzyme is a serine endopeptidase (E.C. 3.4.21.-) such as an enzyme having subtilisin protease activity (EC 3.4.21.62), capable of selectively hydrolyzing the ester of Formula VI.

In some embodiments, an enzyme having subtilisin protease activity, can be a *Bacillus licheniformis* subtilisin A (ABL) or a subtilisin Carlsberg enzyme. In some embodiments, the enzyme is a free enzyme, for example the ABL free enzyme, ALCALASE® (Novozymes A/S, Denmark). In other embodiments, such as that shown in Example 4, the enzyme is crosslinked ABL crystals such as the enzyme sold under the trade name ChiroCLEC-BL (Altus Biologics, Inc., Cambridge, Mass.). In yet other embodiments, the enzyme can be a mixture of enzymes having subtilisin activity (e.g., ALCALASE® and ChiroCLEC-BL). An enzyme having subtilisin protease activity can comprise the amino acid sequence set forth in SEQ ID NO: 1. In some embodiments, variants of SEQ ID NO:1 can be used. Suitable variants include those which retain similar substrate specificity and subtilisin protease activity as SEQ ID NO:1. Other examples of suitable enzymes having subtilisin protease activity include SEQ ID NOs:2-4.

As noted above, wherein it is intended to form the compound of Formula Vb in the stereoisospecific hydrolysis of Formula IV, a compound of Formula Va may also be present in the product mixture. Preferably, the compound of Formula Va is present in a lesser amount than, the compound of Formula Vb. For example, the amount of the compound of Formula Vb produced, i.e., the amount of the (S,S) stereoisomer produced, constitutes at least 60%, 70%, 75%, 80%, 85%, 90%, 93%, 95%, 97%, 98%, 99% or 99.5% of the total amount of the compounds of Formulas Va and Vb produced.

In some embodiments, the present invention further comprises separating the compound of Formula Vb from the compound of Formula IVa. Such separations of carboxylic acids from their corresponding esters are well-known and considered routine in the art. For example, the separation may take advantage of the greater solubility of the acid in aqueous solution, such as by partitioning between an organic solvent and water or an aqueous solution (e.g., a weakly basic aqueous solution). See D. L. Pavia et al., *Introduction to Organic Laboratory Techniques*, 3d ed., Saunders College Publishing: Philadelphia, Pa. (1988), particularly at pages 427-32. Organic solvents commonly used for such partitioning (separation and extraction) are well known to those of ordinary skill in the art, and include solvents such as pentane, hexane, benzene, toluene, petroleum ether, ligroin, ether, methylene chloride, chloroform, carbon tetrachloride, ethyl acetate and the like.

Alternatively, taking advantage of the different reactivities of carboxylic acids and esters (see March and Larock, supra) one of the compounds of Formula Vb or Formula IVa may be transformed into a different compound prior to separation from the other. For example, borane reduces carboxlic acids much more readily than it does esters (see, e.g., March at pages 1544-46). Thus, the mixture could be subjected to reducing conditions using borane that will selectively reduce the compound of Formula Vb to its corresponding alcohol. This alcohol could then be separated from the compound of Formula IVa by standard techniques, such as chromatography. The present invention contemplates any such separation of the compound of Formula IVa, or a compound derived from it, from the compound of Formula Vb, or a compound derived from it, following the selective hydrolysis described above, as "separating the compound of Formula Vb from the compound of Formula IVa" as a means to obtaining stereoisomerically-pure or stereoisomerically-enriched (R,R)— or (S,S)-monatin.

In some embodiments, the present invention further comprises converting the compound of Formula IVa into a compound of Formula Ia:

Ia(R,R)

i.e., into (R,R)-monatin.

In some embodiments, conversion of the compound of Formula IVa into a compound of Formula Ia may be accomplished by
(a) hydrolyzing the compound of Formula IVa to form a compound of Formula VIa:

VIa(R,R)

and
(b) deprotecting the compound of Formula VIa to form a compound of Formula Ia.

Useful reagents for hydrolysis are well known to those of ordinary skill in the art and are described in, e.g., March, supra, particularly at pages 469-74, and Larock, supra, particularly at pages 1959-68. Examples of useful reagents for hydrolysis include Group IA and IIA alkoxides such as LiOH, NaOH, KOH and Ba(OH)$_2$. Other useful reagents include Sm/I$_2$/MeOH and MgI$_2$. Methyl esters may also be cleaved with, e.g., (Na$_2$CO$_3$ or K$_2$CO$_3$)/MeOH/H$_2$O, NaO$_2$/DMSO, KSCN/DMF, EtSH/(AlCl$_3$ or AlBr$_3$), Me$_2$S/(AlCl$_3$ or AlBr$_3$), (Li or Na)SeCH$_3$/DMF, NaCN/HMPA, (LiI or LiBr)/DMF, LiI/(NaOAc or NaCN)/DMF, BCl$_3$, AlI$_3$ or MeSiCl$_3$. Tertiary alkyl esters may be cleaved with, e.g., 2 KOtBu, Mg/MeOH or Me$_3$SiCl/NaI/H$_2$O. Lactones may be cleaved with, e.g., (Li or Na)SMe, KSeO$_3$K or NaSeCH$_2$Ph. In some embodiments, the hydrolysis is accomplished using NaOH in an alcoholic solvent such as MeOH or EtOH. In some embodiments, the hydrolysis is accomplished using KOH in an alcoholic solvent such as MeOH or EtOH.

Useful reagents for deprotection depend on the identity of the protecting group and are well known to those of ordinary skill in the art and are described in, e.g., Greene, supra. For example, the various amino-protecting groups listed above may be removed with one or more of the following: H$_2$/Raney (Ni); H$_2$/Pt, pH 2-4; H$_2$/Pd; H$_2$/Lindlar; and H$_2$/Rh. In some embodiments, the deprotection of a Cbz-protected amino group is accomplished using H$_2$ over Pd/C.

In addition to protecting groups cleaved by hydrogenation, any protecting group for nitrogen that can be cleaved hydrolytically by acid or base, or possibly cleaved by reduction could be employed. Protecting groups cleaved by oxidative methods may be less feasible, owing to the susceptibility of the indole nucleus to oxidation.

Alternatively, conversion of the compound of Formula IVa into a compound of Formula Ia may be accomplished by
(a) deprotecting the compound of Formula IVa to form a compound of Formula VIIIa:

VIIIa and
(b) hydrolyzing the compound of Formula VIIIa to form a compound of Formula Ia. Useful reagents for the hydrolysis and deprotection are as described above for the conversion where hydrolysis is effected before deprotection. However, deprotecting prior to hydrolyzing may result in undesirable lactam formation.

In some embodiments, the present invention further comprises converting the compound of Formula Vb into a compound of Formula Ib:

Ib(S,S)

i.e., into (S,S)-monatin.

In some embodiments, conversion of the compound of Formula Vb into a compound of Formula Ib may be accomplished by
(a) deprotecting the compound of Formula Vb to form a compound of Formula VIIb:

VIIb(S,S)

and
(b) hydrolyzing the compound of Formula VIIb to form a compound of Formula Ib. Useful reagents for hydrolysis and deprotection are as described above for the conversion of a compound of Formula IVa into a compound of Formula Ia.

Alternatively, conversion of the compound of Formula Vb into a compound of Formula Ib may be accomplished by
(a) hydrolyzing the compound of Formula Vb to form a compound of Formula VIb:

VIb and
(b) deprotecting the compound of Formula VIb to form a compound of Formula Ib. Useful reagents for the hydrolysis and deprotection are as described above for the conversion where hydrolysis is effected before deprotection. However, deprotecting prior to hydrolyzing helps suppress undesirable epimerization.

Certain processes of the invention are illustrated in the following examples. While multiple embodiments are disclosed herein, still other embodiments of the present invention may become apparent to those skilled in the art from review of the entirety of this specification. As should be realized from the description herein, the invention is capable of modifications in various aspects, all without departing from the spirit and scope of the present invention. Accordingly, the drawing and entirety of the description are to be regarded as illustrative in nature and not in a limiting sense.

EXAMPLES

Analytical methods. The following methods were used in the examples described below.

Reversed-Phase HPLC:
Column: Varian Microsorb-MV™ 100 Å C18 4.6 mm×150 mm
Mobile Phase: ACN:$H_2O$ (0.1% TFA)=10:90, 6 min; gradient ACN 10% to 90% in 25 min
Retention time: monatin (I) 10.6 min; monatin lactone/methyl ester (III) 13.5 min; Cbz-protected monatin lactone/methyl ester (IV) 18.5 min; (monatin impurity 8.3 min)
Chiral HPLC for all reaction intermediates:
Column: ChiraPak AD, 4.6 mm×250 mm
Mobile Phase Hexane: IPA (0.1% TFA)=60:40; 1 mL/min, monitor at 220 and 273 nm.
Chiral HPLC for monatin:
Column: Chirobiotic T column 4.6×250 mm
Mobile Phase Methanol:AcOH:$NH_4OH$=100:0.2:0.05; 1 mL/min, monitor at 220 and 279 nm.

Example 1

Monatin Methyl Ester Formation

1a. Methylation was done at room temperature in methanol saturated with HCl gas. 100 g Monatin (I) was dissolved in 1.6 L absolutely dry methanol (i.e., at a concentration of about 6% (m/v)) saturated with HCl gas. The mixture was stirred at room temperature for 22 hours. HPLC indicated that the reaction was completed. HCl and solvent were evaporated at room temperature. The residue was subsequently used in Example 2 without purification. The product was a mixture of dimethyl ester (II.1) and lactone/monomethyl ester (III).

1b. The process of 1a may also be carried out with monatin at a concentration of about 10% (m/v) with a reaction time of 2 hours.

Example 2

Carboxybenzoyl Protection

2a. The crude product from Example 1a (mixture of II.1 and III) was dissolved in 1 L ethyl acetate, and then 2.0 L saturated $NaHCO_3$ was added. The pH of this mixture was adjusted to 9.0. At 4° C., 1 equivalent CbzCl (48.9 mL) was added dropwise over a period of 30 minutes. The reaction was done in less than 3 hours. The organic layer was separated, and the aqueous layer was extracted with EtOAc (2×500 mL). The combined EtOAc layers were washed with saturated $NaHCO_3$, dried over $Na_2SO_4$ and evaporated to give 150 g of product (mixture of II.2 and IV).

2b. The process of 2a may also be carried out with a substrate concentration of about 20% (m/v) with a reaction time of 1 hour.

Example 3

Lactonization

3a. The product from Example 2a was dissolved in 300 mL methanol and 300 mL toluene. 7.0 g of TsOH was added. The mixture was stirred at 65° C. for 3 hours. HPLC indicated the lactonization was completed. The solvent was evaporated and the residue was purified by three 1 kg silica gel column eluted with methylene chloride and ethyl acetate (9:1). 85.0 g (yield 58.8% total from starting material, purity 89.0% by RP-HPLC) of (IV, $R^1$ is methyl) was obtained.

3b. The process of 3a is typically carried out in 1:1 methanol:toluene at a substrate concentration of about 25% (m/v), with 10% TsOH added. This process may also be carried out in toluene at a range of substrate concentrations of about 10-20% (m/v) and adding 1% TsOH, which tends to result in less decomposition. Using this process variant, the reaction is run at room temperature for 15 hours, and the product precipitates from toluene, eliminating the need for column chromatography. This process variant typically results in a yield of 70% (from monatin), and the product is 98% pure by HPLC.

Example 4

Enzymatic Hydrolysis

4a. The lactone from Example 3a (IV, $R^1$ is Me, —N(H) Prot is —NHCbz) was dissolved in 640 mL ACN and 2.04 L of phosphate buffer, 0.3 M, pH 7.5. 60 mL CLEC-BL (lot: B103010A) was added. The reaction was stirred at room temperature for 6.5 hours. HPLC indicated that the hydrolysis was close to 50%.

The solution was acidified to pH 2.0, and then extracted with methylene chloride (4×0.7 L). The combined methylene chloride layer was dried over $Na_2SO_4$. The solvent was evaporated. The residue was dissolved in 1.2 L methylene chloride and 1.2 L saturated $NaHCO_3$.

The phase separation was not clear because of aggregation of Vb. The organic phase was separated and the solid-aqueous phase was washed with methylene chloride (2×200 mL). HPLC indicated that the solid still contained over 5% IVa. The aqueous-solid phase was adjusted to pH 2.0, and 500 mL of methylene chloride was added. A milky suspension was formed, and the solid could not be re-dissolved. The pH of this milky suspension was adjusted back to 10. The organic phase was separated. The combined organic phase was washed with 200 mL saturated $NaHCO_3$ and evaporated to give 42 g of IVa (R,R). The solid-aqueous phase was filtered. The solid was dried to give 40.0 g of Vb (S,S) sodium salt.

4b. As noted, the process of 4a was carried out using 85 g starting material. This process may also be carried out on a larger scale, e.g., using 500 g starting material with a reaction time of 19 hours. Methylene chloride (2.5 L) is added followed by filtration to remove the enzyme. The aqueous and organic phases are separated, and the aqueous phase is extracted with methylene chloride (3.25 L). The combined organic phases are used in the next step without any further processing. Alternatively, the combined organic phases are concentrated under reduced pressure to afford a viscous oil. Treatment of the oil with toluene causes precipitation of pure IVa (R,R), but with some loss in yield.

Methylene chloride (2.5 L) is added to the aqueous phase, and the pH is adjusted to 2 using 10% aq. HCl (about 1.5 L). The product Vb (S,S) precipitates and is collected by filtration.

The process of Example 4b is considered preferable to that of 4a, in that certain of the inventors were unable to reproduce the result of Example 4a.

Example 5

Hydrolysis and Hydrogenation to Form Ib

5a. The product Vb from Example 4a was dissolved in 150 mL of ethanol and then 400 mL of 2N NaOH was added. The mixture was stirred at room temperature for 3 hours. HPLC indicated the hydrolysis was completed. The pH of the solution was adjusted to 1.5, extracted with methylene chloride (800 mL and 400 mL). The methylene chloride extractions were dried over $Na_2SO_4$ and evaporated. (To avoid lactonization, the compound was not completely dried.) The diacid VIb was dissolved in 1.6 L of methanol. The solution was purged with $N_2$ gas, then 3.2 g of 10% Pd/C was added. The mixture was purged with $H_2$ gas and then stirred under atmospheric pressure $H_2$ for 3 hours. HPLC indicated that the hydrogenation was completed. The catalyst was filtered off. The solution was concentrated to 400 mL, and then 1.6 L of EtOAc was added while stirring. A white precipitate was formed, which was filtered and dried to give 22.4 g of Ib, i.e., (S,S)-monatin.

5b. The conversion described in Example 5a may also be effected by carrying out the de-protection first, then the hydrolysis. The product Vb is dissolved in MeOH so that the substrate concentration is about 10% (m/v). Pd/C (10% (m/m) of a 50% wet paste of 10% Pd/C) is added, and the mixture is hydrogenated at 3 bar $H_2$ and 40° C. for 1 hour. The mixture is cooled to 25° C., 10% aq. KOH (4 eq.) is added, and the mixture is stirred for 30 minutes. The catalyst is removed by filtration, and the pH is adjusted to 7.5 with AcOH. The mixture is concentrated under reduced pressure and treated with EtOH (to make a 10% solution of monatin in EtOH). A gel forms, which is filtered by Nutsche pressure filtration and dried in a vacuum oven. The remaining precipitate is washed three times with EtOH, and Ib is recovered as the monopotassium salt.

Example 6

Hydrolysis and Hydrogenation to Form Ia

6a. Using the same process described in Example 5a, the product IVa from Example 4a was converted to 20.4 g of Ia, i.e., (R,R)-monatin.

6b. The conversion described in Example 5a (Vb to Ib) may analogously be effected (IVa to Ia). 10% aq. KOH (4 eq.) is added to the product IVa in methylene chloride (5 L) (isolated after enzymatic hydrolysis, such as is described in Example 4b), where the substrate concentration is about 10%, to form a biphasic mixture. The reaction mixture is stirred for 30 minutes at 25° C. The aqueous phase is separated and the pH is adjusted to 8-8.5 using AcOH. MeOH (2.5 L) and Pd/C (10% (m/m) of a 50% wet paste of 10% Pd/C) are added, and the mixture is hydrogenated at 3 bar $H_2$ and 25° C. for 1 hour. The catalyst is removed by filtration, and mixture is concentrated under reduced pressure and treated with EtOH (to make a 10% solution of monatin in EtOH). A gel forms, which is filtered by Nutsche pressure filtration and dried in a vacuum oven. The remaining precipitate is washed three times with EtOH, and Ia is recovered as the monopotassium salt.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entireties.

What is claimed is:

1. A process, comprising:
   (a) reacting a monatin composition comprising S,S and R,R stereoisomeric forms of monatin under conditions suitable for producing ester derivatives of the S,S and R,R stereoisomeric forms of monatin;
   (b) stereospecifically hydrolyzing one of either the S,S ester derivative or R,R ester derivative to form an acid derivative; and,
   (c) separating the ester derivative from the acid derivative, wherein reacting the monatin includes:
   initially forming a diester derivative and a lactone ester derivative of the S,S and R,R stereoisomeric forms of monatin; and
   converting the initially formed diester derivative to the lactone ester derivative of the S,S and R,R stereoisomeric forms of monatin under suitable reaction conditions.

2. The process of claim 1, wherein the S,S ester derivative is stereospecifically hydrolyzed using a protease enzyme.

3. The process of claim 2, wherein said protease enzyme is an enzyme having subtilisin protease activity.

4. The process of claim 3, wherein said protease enzyme is a crosslinked *Bacillus licheniformis subtilisin* A crystal, a *Bacillus licheniformis subtilisin* A free enzyme, or combinations thereof.

5. The process of claim 3, wherein said enzyme is Chiro-CLEC-BL, ALCALASE or combinations thereof.

6. The process of claim 5, wherein the protease enzyme is ChiroCLEC-BL.

7. The process of claim 1, wherein the monatin composition has a concentration ranging from about 6% (m/v) to about 10% (m/v).

8. The process of claim 7, wherein the monatin composition has a concentration of about 10% (m/v).

* * * * *

SEQUENCE LISTING

<160> NUMBER OF SEQ ID NOS: 4

<210> SEQ ID NO 1
<211> LENGTH: 379
<212> TYPE: PRT
<213> ORGANISM: Bacillus licheniformis
<220> FEATURE:
<221> NAME/KEY: VARIANT
<222> LOCATION: (0)...(0)
<223> OTHER INFORMATION: UniProt entry P00780

<400> SEQUENCE: 1

```
Met Met Arg Lys Lys Ser Phe Trp Leu Gly Met Leu Thr Ala Phe Met
 1               5                  10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95
```

```
Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
                180                 185                 190

Ser Leu Tyr Ala Val Lys Val Leu Asn Ser Ser Gly Ser Gly Thr Tyr
            195                 200                 205

Ser Gly Ile Val Ser Gly Ile Glu Trp Ala Thr Thr Asn Gly Met Asp
    210                 215                 220

Val Ile Asn Met Ser Leu Gly Gly Pro Ser Gly Ser Thr Ala Met Lys
225                 230                 235                 240

Gln Ala Val Asp Asn Ala Tyr Ala Arg Gly Val Val Val Val Ala Ala
                245                 250                 255

Ala Gly Asn Ser Gly Ser Ser Gly Asn Thr Asn Thr Ile Gly Tyr Pro
                260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Ser Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
    355                 360                 365

Lys Gly Leu Ile Asn Val Glu Ala Ala Ala Gln
    370                 375

<210> SEQ ID NO 2
<211> LENGTH: 379
<212> TYPE: PRT
<213> ORGANISM: Bacillus licheniformis
<220> FEATURE:
<221> NAME/KEY: VARIANT
<222> LOCATION: (0)...(0)
<223> OTHER INFORMATION: UniProt entry Q45299

<400> SEQUENCE: 2

Met Met Arg Lys Lys Ser Phe Trp Leu Gly Met Leu Thr Ala Phe Met
 1               5                  10                  15

Leu Val Phe Thr Met Ala Phe Ser Asp Ser Ala Ser Ala Ala Gln Pro
                20                  25                  30

Ala Lys Asn Val Glu Lys Asp Tyr Ile Val Gly Phe Lys Ser Gly Val
            35                  40                  45

Lys Thr Ala Ser Val Lys Lys Asp Ile Ile Lys Glu Ser Gly Gly Lys
        50                  55                  60

Val Asp Lys Gln Phe Arg Ile Ile Asn Ala Ala Lys Ala Lys Leu Asp
```

```
            65                  70                  75                  80
Lys Glu Ala Leu Lys Glu Val Lys Asn Asp Pro Asp Val Ala Tyr Val
                    85                  90                  95
Glu Glu Asp His Val Gly His Gly Leu Gly Gln Thr Val Pro Tyr Gly
                    100                 105                 110
Ile Pro Leu Ile Lys Ala Asp Lys Val Gln Ala Gln Gly Phe Lys Gly
                    115                 120                 125
Ala Asn Val Lys Val Ala Val Leu Asp Thr Gly Ile Gln Ala Ser His
                    130                 135                 140
Pro Asp Leu Asn Val Val Gly Gly Ala Ser Phe Val Ala Gly Glu Ala
145                 150                 155                 160
Tyr Asn Thr Asp Gly Asn Gly His Gly Thr His Val Ala Gly Thr Val
                    165                 170                 175
Ala Ala Leu Asp Asn Thr Thr Gly Val Leu Gly Val Ala Pro Ser Val
                    180                 185                 190
Ser Leu Tyr Ala Val Lys Val Leu Asn Ser Ser Gly Ser Gly Ser Tyr
                    195                 200                 205
Ser Gly Ile Val Ser Gly Ile Glu Trp Val Thr Thr Asn Gly Met Asp
                    210                 215                 220
Val Ile Asn Met Ser Leu Gly Gly Ala Ser Gly Ser Thr Ala Met Lys
225                 230                 235                 240
Gln Ala Val Asp Asn Ala Tyr Ala Arg Gly Val Val Val Ala Ala
                    245                 250                 255
Ala Gly Asn Ser Gly Ser Ser Gly Asn Thr Asn Thr Ile Gly Tyr Pro
                    260                 265                 270
Ala Lys Cys Asp Ser Val Ile Pro Val Gly Gly Glu Asp Ser Asn Ser
                    275                 280                 285
Asn Arg Ser Ser Phe Ser Ser Val Gly Ala Glu Leu Glu Val Met Ala
                    290                 295                 300
Pro Val Ser Gly Val Tyr Ser Thr Tyr Pro Thr Asn Thr Tyr Thr Thr
305                 310                 315                 320
Leu Asn Gly Thr Ser Met Ala Ser Pro His Val Ala Gly Thr Ser Ala
                    325                 330                 335
Leu Ile Leu Ser Lys His Pro Asn Leu Ser Ala Ser Gln Val Arg Asn
                    340                 345                 350
Arg Leu Ser Arg Thr Ala Thr Tyr Leu Gly Ser Ser Phe Tyr Tyr Gly
                    355                 360                 365
Lys Gly Leu Ile Asn Val Glu Ala Ala Ala Gln
                    370                 375

<210> SEQ ID NO 3
<211> LENGTH: 379
<212> TYPE: PRT
<213> ORGANISM: Bacillus licheniformis
<220> FEATURE:
<221> NAME/KEY: VARIANT
<222> LOCATION: (0)...(0)
<223> OTHER INFORMATION: UniProt entry Q45300

<400> SEQUENCE: 3

Met Met Arg Lys Lys Ser Phe Trp Leu Gly Met Leu Thr Ala Leu Met
  1               5                  10                  15
Leu Val Phe Thr Met Ala Phe Ser Asp Ser Ala Ser Ala Ala Gln Pro
                    20                  25                  30
Gly Lys Asn Val Glu Lys Asp Tyr Ile Val Gly Phe Lys Ser Gly Val
                    35                  40                  45
```

```
Lys Thr Ala Ser Val Lys Lys Asp Ile Ile Lys Glu Ser Gly Gly Lys
 50                  55                  60

Val Asp Lys Gln Phe Arg Ile Ile Asn Ala Gly Lys Ala Lys Leu Asp
 65                  70                  75                  80

Lys Glu Ala Leu Lys Glu Val Lys Asn Asp Pro Asp Val Ala Tyr Val
                 85                  90                  95

Glu Glu Asp His Val Ala His Val Leu Gly Gln Thr Val Pro Tyr Gly
                100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
        130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Ala Ile Val Ser Gly Ile Glu Trp Ala Thr Thr Thr Gly Met Asp
210                 215                 220

Val Ile Asn Met Ser Leu Gly Gly Ala Ser Val Ser Thr Ala Met Lys
225                 230                 235                 240

Gln Ala Val Asp His Ala Tyr Ala Arg Gly Val Val Val Ser Ser
                245                 250                 255

Ala Gly Asn Ser Gly Ser Ser Gly Asn Thr Asn Thr Ile Gly Tyr Pro
                260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
        290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Thr
            340                 345                 350

Arg Leu Ser Arg Thr Ala Thr Tyr Leu Gly Ser Ser Phe Ser Tyr Gly
        355                 360                 365

Arg Gly Leu Ile Asn Val Glu Ala Ala Ala Gln
    370                 375

<210> SEQ ID NO 4
<211> LENGTH: 379
<212> TYPE: PRT
<213> ORGANISM: Bacillus licheniformis
<220> FEATURE:
<221> NAME/KEY: VARIANT
<222> LOCATION: (0)...(0)
<223> OTHER INFORMATION: UniProt entry Q45301

<400> SEQUENCE: 4

Met Met Arg Lys Lys Ser Phe Trp Phe Gly Met Leu Thr Ala Phe Met
  1               5                  10                  15

Leu Val Phe Thr Met Glu Phe Ser Asp Ser Ala Ser Ala Ala Gln Pro
                 20                  25                  30
```

```
Gly Lys Asn Val Glu Lys Asp Tyr Phe Val Gly Phe Lys Ser Gly Val
         35                  40                  45

Lys Thr Ala Ser Val Lys Lys Asp Ile Ile Lys Glu Ser Gly Gly Lys
 50                  55                  60

Val Asp Lys Gln Phe Arg Ile Ile Asn Ala Ala Lys Ala Thr Leu Asp
 65                  70                  75                  80

Lys Glu Ala Leu Lys Glu Val Lys Asn Asp Pro Asp Val Ala Tyr Val
             85                  90                  95

Glu Glu Asp His Val Ala His Ala Leu Gly Gln Thr Val Pro Tyr Gly
                100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
            130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Phe Ala Val Lys Val Leu Asn Ser Ser Gly Ser Gly Ser Tyr
            195                 200                 205

Ser Gly Ile Val Ser Gly Ile Glu Trp Ala Thr Thr Asn Gly Met Asp
        210                 215                 220

Val Ile Asn Met Ser Leu Gly Gly Pro Ser Gly Ser Thr Ala Met Lys
225                 230                 235                 240

Gln Ala Val Asp Asn Ala Tyr Ser Lys Gly Val Val Pro Val Ala Ala
                245                 250                 255

Ala Gly Asn Ser Gly Ser Ser Gly Tyr Thr Asn Thr Ile Gly Tyr Pro
                260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
        290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
            355                 360                 365

Lys Gly Leu Ile Asn Val Glu Ala Ala Ala Gln
370                 375
```